United States Patent [19]

Tachibana

[11] Patent Number: 4,493,643
[45] Date of Patent: Jan. 15, 1985

[54] DENTAL HANDPIECE HAVING NON-CONTACT ROTATIONAL SPEED DETECTION DEVICE

[75] Inventor: Akifumi Tachibana, Kyoto, Japan

[73] Assignee: Kabushiki Kaisha Morita Seisakusho, Kyoto, Japan

[21] Appl. No.: 454,687

[22] Filed: Dec. 30, 1982

[30] Foreign Application Priority Data

Feb. 9, 1982 [JP] Japan ................... 57-17979

[51] Int. Cl.³ .......................... A61C 1/00; A61C 3/00
[52] U.S. Cl. ..................... 433/27; 433/114; 433/131; 324/174
[58] Field of Search ............... 433/27, 131, 132, 114; 415/10, 503; 324/167, 174

[56] References Cited

U.S. PATENT DOCUMENTS 4,153,993 5/1979 Kataoka et al. ............... 433/132
4,288,746 9/1981 Singbartl .................. 324/174

Primary Examiner—Gene Mancene
Assistant Examiner—Cary E. Stone
Attorney, Agent, or Firm—Koda and Androlia

[57] ABSTRACT

A dental handpiece having therein a non-contact rotating speed detection device which includes an electromagnetic induction pulse generator including a permanent magnet provided close to the rotor in the head of a dental handpiece and a coil wound around the permanent magnet, and a rotor made of a magnetic material provided with recesses and/or projections around its circumference. The handpiece according to the invention facilitates to accurately detect rotor speed by detecting a pulse voltage proportionate to the rotation speed and therefore is useful for dental treatment and experiments.

5 Claims, 6 Drawing Figures

DENTAL HANDPIECE HAVING NON-CONTACT ROTATIONAL SPEED DETECTION DEVICE

BACKGROUND OF THE INVENTION

1. Field of the Invention

The present invention relates to a dental handpiece having therein non-contact rotational speed detection device.

2. Prior Art

For dental treatment, a tool tip on the head of a handpiece is rotated at a high speed. However, when cutting load increases, rotating speed is usually reduced significantly. To know the rotating speed under load is desirable for proper treatment, useful for data analysis of clinical experiments, and necessary to control the rotating speed at a constant value. For these purposes, prior art attempts to detect the rotating speed of the motor for a micro-motor driven handpiece were based upon motor drive voltage or current. However, this attempt has not been successful since the rotating speed is detected indirectly via voltage or current, and thus large errors are caused. The magnetic speed detection system, which was recently developed by the applicant and has been used for pneumatic handpieces, includes a magnetic resistance device or a Hall effect element as a detection means and generates a pulse voltage using a magnetic resistance effect caused by the rotation of the rotor, a part of which is magnetized or in which a small permanent magnet piece is imbedded. In the system, the rotor is very small, and incorporates a chuck mechanism to hold a cutting tool. However, it is very difficult to imbed a magnet piece in the rotor. When magnetizing the rotor, the material of the rotor must be specially selected. Furthermore, bearings made of a non-magnetic material must be used to easily detect changes in the magnetic flux; therefore, bearings made of ordinary magnetic metal cannot be used. This is a fatal defect of the magnetic speed detection device.

SUMMARY OF THE INVENTION

It is therefore an object to the present invention to provide a dental handpiece free from the problems or drawbacks as above. This object is achieved by a non-contact rotating speed detection device which comprises an electromagnetic induction pulse generator including a permanent magnet provided close to the rotor in the head of a dental handpiece and a coil wound around the permanent magnet unit. The rotor made of a magnetic material is provided with the recesses and/or projections around its circumference, whereby the magnetic flux crossing the coil is changed according to changes in the magnetic resistance of the magnetic circuit composed of the pulse generator and the rotor when the rotor rotates, and thus the electromagnetic induction pulse generator generates an induction voltage proportionate to the product of the number of the projections or recesses and the rotating speed.

BRIEF DESCRIPTION OF THE DRAWINGS

The present invention will be seen by reference to the description, taken in connection with the accompanying drawings, wherein like numerals indicate like elements and in which.

DETAILED DESCRIPTION OF THE INVENTION

Figure 1A:
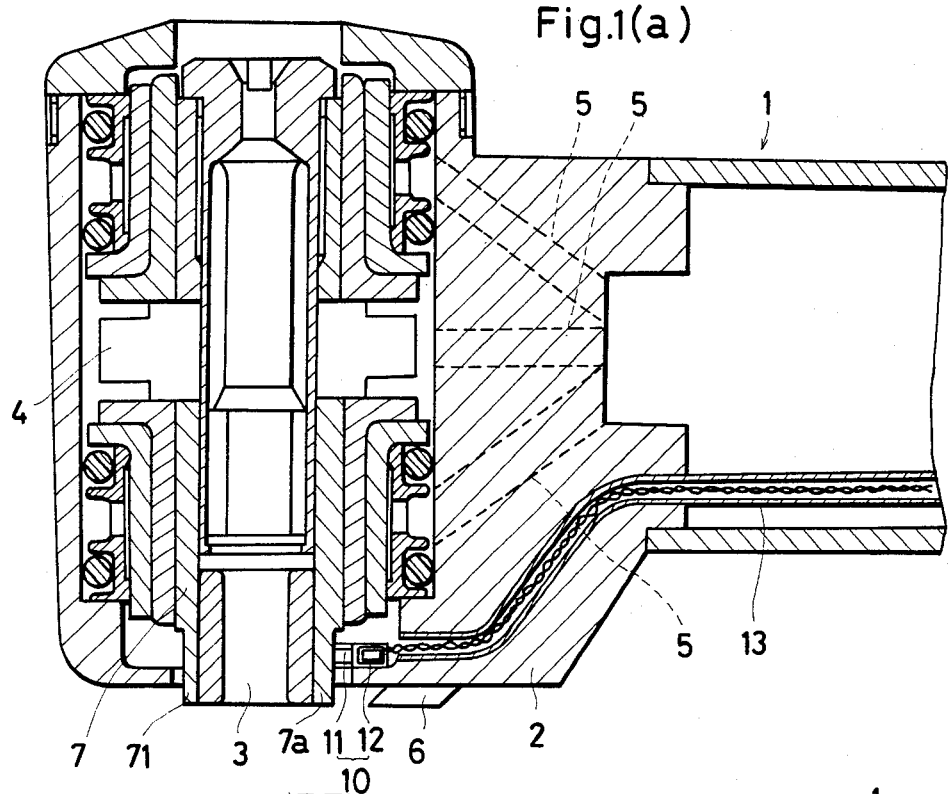
FIG. 1(a) is a cutaway side view of the major section of the handpiece using pneumatic bearings in accordance with the invention.
Figure 1B:
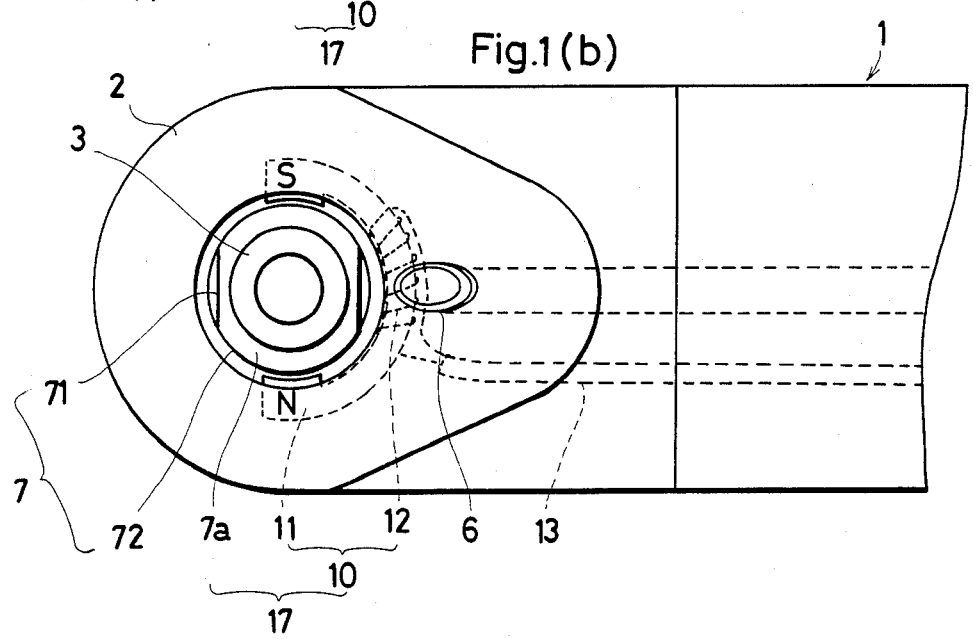
FIG. 1(b) is a bottom view of the device of FIG. 1(a)
Figure 2A:
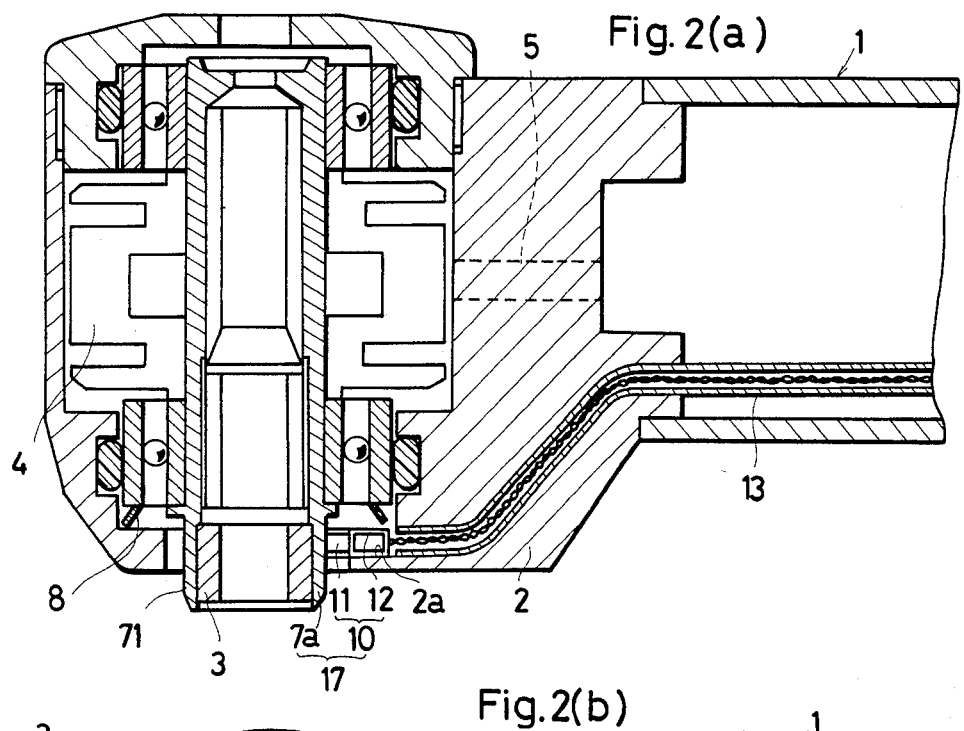
FIG. 2(a) is a cutaway side view of the major section of the handpiece using ball bearings in accordance with the invention.
Figure 2B:
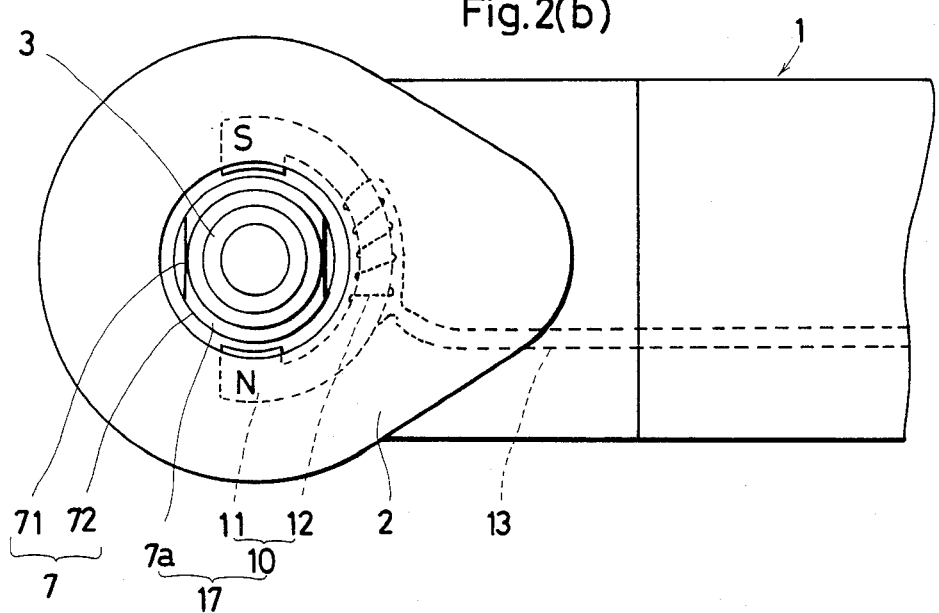
FIG. 2(b) is a bottom view of the device of FIG. 2(a)

Referring to FIGS. 1(a) and 1(b), drawings of an embodiment of the present invention applied to a known pneumatic handpiece using pneumatic bearings, 1 is a handpiece, 2 is a head, 3 is a front guide being pressure-fit into a rotor shaft 7a, 4 is an impeller on the rotor shaft 7a, 5 is a nozzle which supplies air to the impeller 4 and bearings, and 6 is a water nozzle. The rotor 7 is made of a magnetic material, such as carbon steel. At the end 7a of the rotor, chamfered section 71 (corresponding to the recesses on the rotor) are symmetrically formed on both sides to which a spanner is engaged when a tool chip is mounted or dismounted. Since the circumferential surface at the end 7a of the rotor is discontinued by the chamfered sections 71, the air gaps at the chamfered sections are larger than those at the circumferential section 72. The head 2 is made of a non-magnetic material such as brass. In the head, a semicircular permanent magnet unit 11 with a coil 12 wound at its central section is fixed with an adhesive so that its N and S poles are placed opposite to each other close to the rotor's end 7a, symmetrically in reference to the rotation axis center. (The magnet unit for the handpiece using ball bearings shown in FIG. 2(a) and FIG. 2(b) can also be fixed with an adhesive. It can also be fixed in a groove 2(a) by a coned disc spring 8 which is used to fix the outer race of the bearing.) The non-contact rotating speed detection device 17 of the present invention comprises an electromagnetic induction type pulse generator 10 composed of the permanent magnet unit with the coil 12 wound at its central section, and the rotor 7 which is made of a magnetic material and equipped with discontinuities such as the recesses 71 and projections 72 on its circumferential surface. The pulse generator 10 and the rotor 7 form a magnetic circuit. When the rotor 7 is driven, the magnetic resistance of the magnetic circuit is changed twice per rotation by the effect of the chamfered sections 71 corresponding to the recesses, and thus the magnetic flux passing through the permanent magnet unit 11 is also changed twice. Accordingly, pulse voltage whose frequency is proportionate to the number of the chamfered sections 71 and rotating speed is induced in the coil 12. This electrical pulse signal is used to accurately detect the rotating speed of the rotor 7. The electrical signal is picked up by the lead wires passing through a stainless steel pipe 13 imbedded in the head 2, and electrically processed to display, record and control the rotating speed. FIGS. 2(a) and 2(b) are drawings of an embodiment of the present invention applied to a known pneumatic handpiece using ball bearings. Since the basic construction of the embodiment in FIGS. 2(a) and 2(b) is the same as that of the embodiment in FIGS. 1(a) and 1(b), the corresponding parts between the two embodiments are represented by the identical numbers, and the detailed description of the latter embodiment is omitted.

Figure 3:
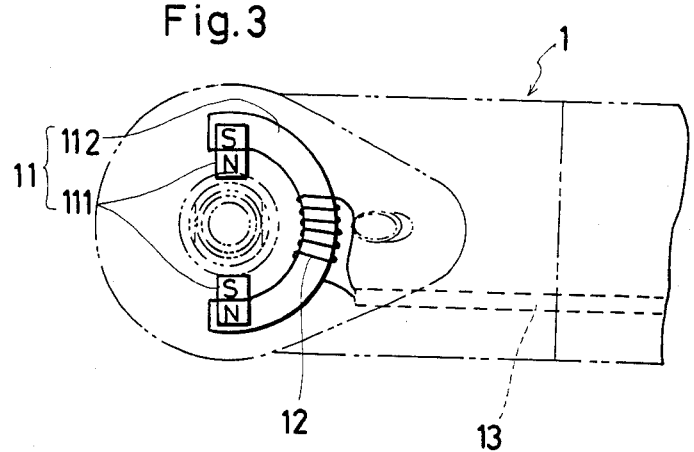
FIG. 3 is a bottom view of a permanent magnet unit including permanent magnet pieces at both ends of a semicircular magnetic element of another embodiment of the invention.
Figure 4:
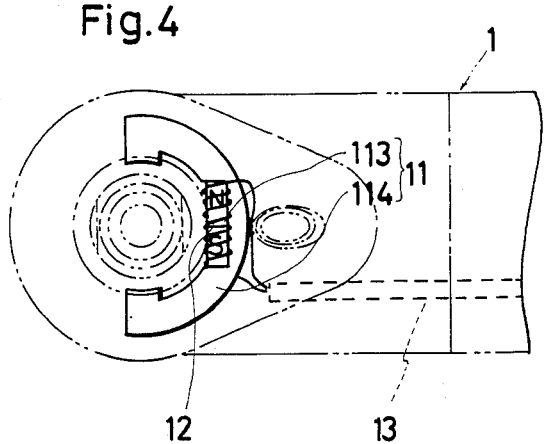
FIG. 4 is a bottom view of a permanent magnet unit including a permanent magnet piece at the center of a semicircular magnetic element of a further embodiment of the invention.

FIGS. 3 and 4 show the permanent magnet unit 11 to be built in the embodiment of the present invention. Referring to FIG. 3, flat permanent magnet pieces 111 are fixed at both ends of the semicircular magnet element 112 so that the N and S poles are placed opposite to each other symmetrically in reference to the rotation axis center of the rotor 7. Referring to FIG. 4, a bar-shaped permanent magnet element 113 is built in the central section of a semicircular magnet element 114 whose ends are also positioned opposite to each other symmetrically in reference to the rotation axis center. When these permanent magnet elements 111 and 113 are combined with magnetic elements 112 and 114, the cost of the magnet unit can be reduced further. As described above, the rotating speed detection device of the present invention provides a rotating speed detector 17 composed of an electromagnetic induction pulse generator 10 located close to the rotor 7 in the head 2 of the handpiece 1 to detect the pulse voltage signal which accurately corresponds to the rotating speed of the rotor. The device can be embodied in various handpieces, such as a straight type whose output shaft is installed in the longitudinal direction of the handpiece, regardless of drive methods; electrical drive method or pneumatic drive method. The rotor 7 does not need to be magnetized or equipped with magnets. Non-magnetic bearings are not required. As a result, the system is simple, inexpensive and durble. Furthermore, the device can accurately detect rotating speed under load and is effectively used for dental training, clinical experiments and treatments and various controls.

I claim:

1. A dental handpiece having therein a non-contact rotational speed detection device, which device comprises:
   cylindrical rotor made of a magnetic material provided with discontinuities around its circumference: and
   an electromagnetic induction pulse generator comprising a permanent magnet provided close to said cylindrical rotor in a head of said dental handpiece and a coil wound around said permanent magnet, whereby the pulse generator generates an induction voltage proportionate to the product of the number of said discontinuities and the rotational speed;

2. A dental handpiece as claimed in claim 1, wherein said discontinuities are a pair of chamfered sections formed symmetrically relative to the rotational axis center at a lower end portion of said cylindrical rotor and wherein said permanent magnet has a semicircular shape, includes said coil would around a central section so that the N and S poles are symmetrical relative to the rotor axis center, and is provided close to the circumference of said lower end portion.

3. A dental handpiece as claimed in claim 1, wherein projections are provided on a circumferential section of a lower end portion of said cylindrical rotor and wherein said permanent magnet has a semicircular shape, includes said coil wound around a central section so that the N and S poles are symmetrical relative to the rotor axis center, and is provided close to the circumference of said lower end portion.

4. A dental handpiece as claimed in claim 2 or 3, wherein said permanent magnet is fixed in the head with an adhesive.

5. A dental handpiece as claimed in claim 2 or 3, wherein said permanent magnet is fixed in the head by a coned disc spring.

* * * * *